United States Patent

Hoshino

[11] Patent Number: 6,146,661
[45] Date of Patent: *Nov. 14, 2000

[54] CHEWABLE TABLET

[75] Inventor: Kazuaki Hoshino, Tokyo, Japan

[73] Assignee: Chugai Seiyaku Kabushiki Kaisha, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 09/043,606
[22] PCT Filed: Oct. 3, 1996
[86] PCT No.: PCT/JP96/02869
  § 371 Date: Mar. 24, 1998
  § 102(e) Date: Mar. 24, 1998
[87] PCT Pub. No.: WO97/12606
  PCT Pub. Date: Apr. 10, 1997

[30] Foreign Application Priority Data

Oct. 3, 1995 [JP] Japan .................................... 7-291612

[51] Int. Cl.$^7$ ...................................................... A61K 9/20
[52] U.S. Cl. .......................... 424/465; 424/439; 424/441; 424/464; 424/474
[58] Field of Search ...................................... 424/464, 465, 424/474, 439, 441

[56] References Cited

U.S. PATENT DOCUMENTS 5,013,557  5/1991  Tai .......................................... 424/493

FOREIGN PATENT DOCUMENTS

| 4-91029 | 3/1992 | Japan . |
| 5-310558 | 11/1993 | Japan . |
| 88/08704 | 11/1988 | WIPO . |
| WO 88/08704 | 11/1988 | WIPO . |
| 92/17161 | 10/1992 | WIPO . |
| WO 92/17161 | 10/1992 | WIPO . |

*Primary Examiner*—Michael A. Williamson
*Attorney, Agent, or Firm*—Browdy and Neimark

[57] ABSTRACT

Chewable tablets prepared by incorporating a sugar alcohol with a dissolution endotherm of 20 calories or more per gram of a gastrointestinally active ingredient such as a mucous membrane repairing agent or an antacid are provided. The chewable tablets enable the gastrointestinally active ingredient to be orally administered with ease, without water and free from displeasing intrabuccal sensations characteristic of a gastrointestinally active ingredient.

4 Claims, No Drawings

CHEWABLE TABLET

This application is a 371 of PCT/JP96/02869 filed Oct. 3, 1996.

TECHNICAL FIELD

The present invention relates to chewable tablets as a gastrointestinal drug. More particularly, the invention concerns chewable tablets which have solved the problem of poor intrabuccal sensations by incorporating a sugar alcohol in a certain amount or more.

BACKGROUND ART

Chewable tablets are taken slowly by chewing or sucking in the mouth, and enable a pharmaceutical contained therein to be orally administered without water. Chewable tablets now on the market, however, may cause discomfort (e.g. roughness or dustiness) during or after ingestion, posing the problem of poor intrabuccal sensations. Particularly when a metal salt such as a calcium, magnesium or aluminum salt is incorporated, a marked discomfort arises. This is a serious problem for chewable tablets which remain in the mouth for a long time as compared with other preparations. By contrast, success in improving the sensations during or after ingestion were achieved by adjusting the particle sizes of the ingredients incorporated (Japanese Laid-Open Patent Publication No. 203332/89). This measure is not highly preferred for manufacture, because it increases the number of manufacturing steps. Poor intrabuccal sensations due to a calcium salt were also relieved by containing low viscosity hydroxyalkyl cellulose and high viscosity hydroxyalkyl cellulose (Japanese Laid-Open Patent Publication No. 306229/93). However, the effect obtained is not entirely satisfactory. Attempts have been made to improve the intrabuccal sensations by combining various additives such as sweeteners, acidic ingredients, taste correctives, polymeric compounds and essential oils of crude drugs. In such cases, the additive is needed in an amount of not less than 1.5 to 2 times the amount of the gastrointestinally active ingredient, thus making the size of the chewable table itself large. Such large tablets are difficult to take. In addition, a special machine for producing large tablets is required, posing an economic problem.

As described above, gastrointestinal chewable tablets thus far known have been unsatisfactory in intrabuccal sensations, and there has been a demand for correcting such a drawback.

DISCLOSURE OF THE INVENTION

We, the inventors, have conducted in-depth studies to improve the intrabuccal sensations characteristic of chewable tablets as a gastrointestinal drug. These studies have found that this objective can be attained by incorporating not less than a specific amount of a sugar alcohol into the gastrointestinally active ingredient; such a finding led us to accomplish the present invention.

That is, this invention concerns chewable tablets containing a sugar alcohol with a dissolution endotherm of 20 calories or more per gram of a gastrointestinally active ingredient.

The gastrointestinally active ingredient used in the invention may be any pharmaceutically active ingredient for a gastrointestinal drug, such as a mucous membrane repairing agent or an antacid. The particle size of the starting material for the gastrointestinal drug should desirably be small, but any commercially available grade poses no problem. The gastrointestinally active ingredient may be a single ingredient or a mixture of two or more ingredients.

Examples of the mucous membrane repairing agent are sucralfate, sodium azulene sulfonate, aldioxa, glycyrrhizic acid and its salts, L-glutamine, copper chlorophyllin potassium, histidine hydrochloride, porcine gastric wall pepsin decomposition product, and methylmethionine sulfonium chloride.

The antacid includes not only a common antacid generally recognized as being effective in neutralizing gastric acid, but also an $H_2$ receptor blocking antisecretory effective in healing the gastrointestinal tract. Examples of the antacid are sucralfate, dried aluminum hydroxide gel, magnesium aluminosilicate, magnesium silicate, synthetic aluminum silicate, synthetic hydrotalcite, magnesium oxide, magnesia alumina hydrate, aluminum hydroxide gel, magnesium hydroxide, sodium bicarbonate, magnesium carbonate, precipitated calcium carbonate, magnesium aluminometasilicate, anhydrous calcium hydrogenphosphate, and calcium hydrogenphosphate. Examples of the $H_2$ receptor blocking antisecretory are ranitidine, cimetidine, famotidine, nizatidine and roxatidine acetate.

The sugar alcohol used in the invention may be any sugar alcohol in common use, such as sorbitol, erythritol, xylitol or mannitol. The dissolution endotherm of any of the various sugar alcohols is 24 cal/g for sorbitol, 43 calg for erythritol, 35 cal/g for xylitol, or 29 cal/g for mannitol (measured in accordance with the customary method by accurately weighing about 0.5 g of the sugar alcohol, and dissolving it in 20 ml of distilled water at 25° C.).

These sugar alcohols may be used alone or as a mixture of two or more. Any of them is incorporated in such an amount that the dissolution endotherm will be 20 cal or more per gram of the gastrointestinally active ingredient, whereby gastrointestinal chewable tablets with satisfactory intrabuccal sensation when orally administered can be produced. In the chewable tablets of the invention, the amount of the sugar alcohol incorporated is determined by calculation such that it gives a dissolution endotherm of 20 cal or more per gram of the gastrointestinally active ingredient as described above. The upper limit of the amount of the sugar alcohol incorporated in one chewable tablet is restricted by the size of the tablet and the contents of the ingredients other than the sugar alcohol, including the gastrointestinally active ingredient, in one tablet. Assume that 500 mg of a gastrointestinally active ingredient, 5 mg of an excipient, and 5 mg of a binder are contained, with the rest being xylitol (the sugar alcohol used in the invention), are used in the preparation of 1 g of a chewable tablet in accordance with the invention. In this case, the amount of xylitol incorporated is 490 mg. The dissolution endotherm of the sugar alcohol in the chewable tablet is calculated at 34.3 cal per gram of the gastrointestinally active ingredient.

As noted above, the lower limit of the amount of the sugar alcohol incorporated in the invention is 20 cal as a dissolution endotherm per gram of the gastrointestinally active ingredient in the chewable tablet. Whereas its upper limit is not restricted as far as it is within the range in which chewable tablets can be molded. Within this range, it is possible to select the type and the amount of incorporation of the sugar alcohol in view of the hygroscopicity, sweetness, melting point, price, and so forth. The amount of the sugar alcohol incorporated varies with the type of the gastrointestinally active ingredient used. In the case of a gastrointestinally active ingredient, such as sucralfate, which is incorporated in a high proportion, for example, the amount of the sugar alcohol incorporated expressed in terms of the dissolution endotherm is about 20 to 200 cal, preferably about 20 to 100 cal, per gram of sucralfate. On the other hand, in the case of a gastrointestinally active ingredient, such as azulene, which is incorporated in a low proportion, that amount as the dissolution endotherm is about 20 to 30,000 cal, preferably about 500 to 20,000 cal, per gram of azulene.

For the preparation of the chewable tablets of the invention, additives for use in the production of ordinary tablets may be used, unless they do harm, in addition to the gastrointestinally active ingredient and the sugar alcohol. Examples are pharmaceutically acceptable excipients, binders, lubricants, preservatives, stabilizers, colorants and flavors.

The weight of the chewable tablet of the invention is not restricted. For administration of one tablet once, for instance, the weight of one tablet is preferably about 0.5 to 2.0 g, more preferably 0.8 to 1.5 g.

The method of preparing the chewable tablet of the invention is not restricted, either. An ordinary method for producing tablets can be applied.

EXAMPLES

The present invention will be illustrated in further detail with reference to the following Preparation Examples and Testing Examples, but the invention is in no way restricted by their descriptions.

Preparation Example 1

| Sucralfate | 500 mg |
| Xylitol | 300 mg |
| Aspartame | 4 mg |
| Magnesium stearate | 10 mg |
| Herb flavor | 1 mg |

These ingredients were mixed, kneaded, dried, and then tableted to obtain chewable tablets (diameter 14 mm). The dissolution endotherm of the sugar alcohol per gram of the gastrointestinally active ingredient was 21 cal.

Preparation Example 2

| Sucralfate | 500 mg |
| Synthetic hydrotalcite | 250 mg |
| Mannitol | 250 mg |
| Erythritol | 350 mg |
| Aspartame | 3 mg |
| Magnesium stearate | 10 mg |
| Menthol flavor | 1 mg |

These ingredients were mixed, and treated in the same way as in the Preparation Example 1 to obtain chewable tablets (diameter 18 mm). The dissolution endotherm of the sugar alcohols per gram of the gastrointestinally active ingredient was 29.7 cal.

Preparation Example 3

| Sucralfate | 500 mg |
| Sodium azulene sulfonate | 2 mg |
| L-glutamine | 140 mg |
| Magnesium aluminometasilidate | 200 mg |
| Mannitol | 200 mg |
| Xylitol | 350 mg |
| Aspartame | 3 mg |
| Magnesium stearate | 10 mg |
| Herb flavor | 1 mg |

These ingredients were mixed, and treated in the same way as in the Preparation Example 1 to obtain chewable tablets (diameter 18 mm). The dissolution endotherm of the sugar alcohols per gram of the gastrointestinally active ingredient was 21.4 cal.

For comparison of intrabuccal sensations with the pharmaceutical composition of the present invention, Comparative Examples are offered. In these Comparative Examples, other sweeteners (sucrose and lactose) were used in place of the sugar alcohols. Alternatively, the sweetener and the sugar alcohol (the dissolution endotherm per gram of the gastrointestinally active ingredient: less than 20 cal) were concomitantly used. Under these conditions, chewable tablets were produced so as to have sweetness, diameter, weight and hardness comparable to those of the pharmaceutical compositions obtained in the Preparation Examples. The sweetness was adjusted using the values shown in Table 1.

TABLE 1

Sweetness of the various sugars and sugar alcohols (sweetness of sucrose: 1.0)

| Sugar | Sweetness |
| --- | --- |
| Sucrose | 1.0 |
| Lactose | 0.2 |
| Mannitol | 0.5 |
| Xylitol | 0.9 |
| Erythritol | 0.7 |

Comparative Example 1

| Sucralfate | 500 mg |
| Sucrose | 260 mg |
| Lactose | 40 mg |
| Aspartame | 4 mg |
| Magnesium stearate | 10 mg |
| Herb flavor | 1 mg |

These ingredients were mixed, and treated In the same way as in the Preparation Example 1 to obtain chewable tablets (diameter 14 mm). No sugar alcohol was incorporated.

Comparative Example 2

| Sucralfate | 500 mg |
| Synthetic hydrotalcite | 250 mg |
| Sucrose | 320 mg |
| Lactose | 280 mg |

-continued

|  |  |
|---|---|
| Aspartame | 3 mg |
| Magnesium stearate | 10 mg |
| Menthol flavor | 1 mg |

These ingredients were mixed, and treated in the same way as in the Preparation Example 1 to obtain chewable tablets (diameter 18 mm). No sugar alcohol was incorporated.

Comparative Example 3

|  |  |
|---|---|
| Sucralfate | 500 mg |
| Sodium azulene sulfonate | 2 mg |
| L-glutamine | 140 mg |
| Magnesium aluminometasilicate | 200 mg |
| Sucrose | 380 mg |
| Lactose | 170 mg |
| Aspartame | 3 mg |
| Magnesium stearate | 10 mg |
| Herb flavor | 1 mg |

These ingredients were mixed, and treated in the same way as in the Preparation Example 1 to obtain chewable tablets (diameter 18 mm). No sugar alcohol was incorporated.

Comparative Example 4

|  |  |
|---|---|
| Sucralfate | 500 mg |
| Xylitol | 250 mg |
| Sucrose | 44 mg |
| Lactose | 6 mg |
| Aspartame | 4 mg |
| Magnesium stearate | 10 mg |
| Herb flavor | 1 mg |

These ingredients were mixed, and treated in the same way as in the Preparation Example 1 to obtain chewable tablets (diameter 14 mm). The dissolution endotherm of the sugar alcohol per gram of the gastrointestinally active ingredient was 17.5 cal.

Comparative Example 5

|  |  |
|---|---|
| Sucralfate | 500 mg |
| Sodium azulene sulfonate | 2 mg |
| L-glutamine | 140 mg |
| Magnesium aluminometasilicate | 200 mg |
| Mannitol | 170 mg |
| Xylitol | 300 mg |
| Sucrose | 55 mg |
| Lactose | 25 mg |
| Aspartame | 3 mg |
| Magnesium stearate | 10 mg |
| Herb flavor | 1 mg |

These ingredients were mixed, and treated in the same way as in the Preparation Example 1 to obtain chewable tablets (diameter 18 mm). The dissolution endotherm of the sugar alcohols per gram of the gastrointestinally active ingredient was 18.3 cal.

Testing Examples Organoleptic Test Methods:

Testing Example 1

Organoleptic test was done on 32 subjects (men and women) aged 22 to 58 years to compare the pharmaceutical composition of the present invention shown in the Preparation Example 1 and the control pharmaceutical composition shown in the Comparative Example 1. The testing involved orally administering the pharmaceutical composition of the invention and the control pharmaceutical composition to the respective subjects, and asking them which of the pharmaceutical compositions they preferred, or whether they felt any difference existed between the two pharmaceutical compositions.

Testing Example 2

The pharmaceutical composition of the Preparation Example 2 and the pharmaceutical composition of the Comparative Example 2 were compared in the same manner as in the Testing Example 1.

Testing Example 3

The pharmaceutical composition of the Preparation Example 3 and the pharmaceutical composition of the Comparative Example 3 were compared in the same manner as in the testing Example 1.

Testing Example 4

The pharmaceutical composition of the Preparation Example 1 and the pharmaceutical composition of the Comparative Example 4 were compared in the same manner as in the Testing Example 1.

Testing Example 5

The pharmaceutical composition of the Preparation Example 3 and the pharmaceutical composition of the Comparative Example 5 were compared in the same manner as in the Testing Example 1.

The results are shown in Table 2.

TABLE 2

Results of Sensory Testing

| Testing Example | Pharmaceutical composition of the invention preferred | No difference | Control pharmaceutical composition preferred |
|---|---|---|---|
| 1 | 25 subjects (78%) | 5 subjects (16%) | 2 subjects (6%) |
| 2 | 23 subjects (72%) | 9 subjects (28%) | 0 subject (0%) |
| 3 | 23 subjects (72%) | 8 subjects (25%) | 1 subject (3%) |
| 4 | 20 subjects (63%) | 11 subjects (34%) | 1 subject (3%) |
| 5 | 21 subjects (66%) | 11 subjects (34%) | 0 subject (0%) |

Discussion:

As seen from Table 2, clearly more subjects preferred the pharmaceutical composition of the invention to the control pharmaceutical composition. Such an outcome obtained despite identical of the sweetness, diameter, weight and hardness, shows that there was a clear difference in intrabuccal sensations between the two pharmaceutical compositions. Thus, the pharmaceutical composition of the invention produces superior intrabuccal sensations.

INDUSTRIAL APPLICABILITY

The chewable tablets of the present invention are markedly improved in respect to intrabuccal sensations characteristic of a gastrointestinal drug. These tablets are very useful as a pharmaceutical containing a gastrointestinal drug substance.

I claim:

1. A chewable tablet as a gastrointestinal drug composition in the form of a chewable tablet which contains erythritol or a mixture of erythritol and another sugar alcohol, and a gastrointestinally active ingredient, the amount of erythritol or the mixture of erythritol and said sugar alcohol expressed in terms of the dissolution endotherm per gram of the active ingredient being at least 20 cal, wherein the gastrointestinally active ingredient is at least one of a mucous membrane repairing agent selected from the group consisting of sucralfate, sodium azulene sulfonate, aldioxa, glycyrrhizic acid and its salts, L-glutamine, copper chlorophyllin potassium, histidine hydrochloride, porcine gastric wall pepsin decomposition product, and methylmethionine sulfonium chloride, an antacid selected from the group consisting of fried aluminum hydroxide gel, magnesium aluminosilicate, magnesium silicate, synthetic aluminum silicate, synthetic hydrotalcite, magnesium oxide, magnesia alumina hydrate, aluminum hydroxide gel, magnesium hydroxide, sodium bicarbonate, magnesium carbonate, precipitated calcium carbonate, magnesium aluminometasilicate, anhydrous calcium hydrogenphosphate, and calcium hydrogenphosphate, or an $H_2$ receptor blocking antisecretory selected from the group consisting of ranitidine, cimetidine, famotidine, nizatidine and roxatidine acetate.

2. A chewable tablet as a gastrointestinal drug composition in the form of a chewable tablet which contains erythritol or a mixture of erythritol and another sugar alcohol, and sucralfate, the amount of erythritol in terms of the dissolution endotherm gram of said sucralfate being at least 20 cal.

3. The chewable tablet according to claim 1, wherein said other sugar alcohol of the mixture is present and is selected from the group consisting of sorbitol, xylitol and mannitol.

4. The chewable tablet according to claim 2, wherein said other sugar alcohol of the mixture is present and is selected from the group consisting of sorbitol, xylitol and mannitol.

* * * * *

UNITED STATES PATENT AND TRADEMARK OFFICE
CERTIFICATE OF CORRECTION

PATENT NO.    : 6,146,661
DATED         : November 14, 2000
INVENTOR(S)   : Kazuaki Hoshino It is certified that error appears in the above-identified patent and that said Letters Patent is hereby corrected as shown below:

<u>Column 2,</u>
Line 29, delete "43 calg" and insert therefor -- 43 cal/g --;

<u>Column 7,</u>
Line 27, delete "fried" and insert therefor -- dried --.

Signed and Sealed this

Fourth Day of December, 2001

Attest:

*Nicholas P. Godici*

NICHOLAS P. GODICI
*Attesting Officer*     *Acting Director of the United States Patent and Trademark Office*